(12) United States Patent
Konofagou et al.

(10) Patent No.: US 11,577,096 B2
(45) Date of Patent: Feb. 14, 2023

(54) SYSTEMS AND METHODS FOR MODULATION AND MAPPING OF BRAIN TISSUE USING AN ULTRASOUND ASSEMBLY

(71) Applicant: THE TRUSTEES OF COLUMBIA UNIVERSITY IN THE CITY OF NEW YORK, New York, NY (US)

(72) Inventors: Elisa E. Konofagou, New York, NY (US); Gesthimani Samiotaki, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 1293 days.

(21) Appl. No.: 15/858,247

(22) Filed: Dec. 29, 2017

(65) Prior Publication Data

US 2018/0140871 A1    May 24, 2018

Related U.S. Application Data

(63) Continuation of application No. PCT/US2016/040776, filed on Jul. 1, 2016.
(Continued)

(51) Int. Cl.
*A61N 7/00* (2006.01)
*A61B 17/225* (2006.01)
(Continued)

(52) U.S. Cl.
CPC .............. *A61N 7/00* (2013.01); *A61B 8/0808* (2013.01); *A61B 8/42* (2013.01); *A61B 8/4254* (2013.01);
(Continued)

(58) Field of Classification Search
None
See application file for complete search history.

(56) References Cited

U.S. PATENT DOCUMENTS

| 8,097,926 B2 * | 1/2012 | De Graff .................. A61B 8/12 |
| | | 257/419 |
| 9,061,133 B2 | 6/2015 | Wurster et al. |
| (Continued) | | |

FOREIGN PATENT DOCUMENTS

| WO | WO 2014/160964 A1 | 10/2014 | |
| WO | WO 2015/200576 | * 12/2015 | ............... A61N 7/00 |

OTHER PUBLICATIONS

International Search Report dated Sep. 9, 2016 in International Application No. PCT/US2016/040776.
(Continued)

*Primary Examiner* — Luther Behringer
(74) *Attorney, Agent, or Firm* — Baker Botts L.L.P.

(57) ABSTRACT

Methods and systems for modulation and mapping of brain tissue in a subject using an ultrasound assembly are provided. An exemplary method for modulation uses an ultrasound assembly including a housing and an ultrasound transducer joined to the housing. The method includes securing the housing to the head of the subject with the ultrasound transducer aligned with a region of the brain tissue to target the region of the brain tissue for modulating, and providing focused ultrasound at an acoustic pressure to the targeted region using the ultrasound transducer to induce cavitation proximate the targeted region. The method further includes detecting a cavitation signal magnitude from the induced cavitation corresponding to the acoustic pressure and modulating the targeted region.

4 Claims, 16 Drawing Sheets

Related U.S. Application Data

(60) Provisional application No. 62/187,639, filed on Jul. 1, 2015.

(51) Int. Cl.
  *A61B 8/00* (2006.01)
  *A61B 8/08* (2006.01)
  *G01S 7/52* (2006.01)
  *A61B 8/13* (2006.01)
  *A61B 5/00* (2006.01)

(52) U.S. Cl.
  CPC .......... *A61B 8/4427* (2013.01); *A61B 8/4477* (2013.01); *A61B 8/481* (2013.01); *A61B 8/5261* (2013.01); *A61B 8/5269* (2013.01); *A61B 17/225* (2013.01); *G01S 7/52041* (2013.01); *A61B 5/0036* (2018.08); *A61B 8/0833* (2013.01); *A61B 8/13* (2013.01); *A61B 8/4281* (2013.01); *A61N 2007/0026* (2013.01); *A61N 2007/0039* (2013.01); *A61N 2007/0052* (2013.01); *A61N 2007/0065* (2013.01); *A61N 2007/0073* (2013.01); *A61N 2007/0078* (2013.01); *A61N 2007/0095* (2013.01)

(56) References Cited

U.S. PATENT DOCUMENTS

| | | | |
|---|---|---|---|
| 9,743,909 B1* | 8/2017 | Sapozhnikov | A61B 5/0062 |
| 10,350,439 B2* | 7/2019 | Maxwell | A61N 7/02 |
| 2003/0130599 A1* | 7/2003 | Restle | A61B 17/22029 601/2 |
| 2009/0005711 A1 | 1/2009 | Konofagou et al. | |
| 2009/0221902 A1* | 9/2009 | Myhr | A61N 7/02 601/2 |
| 2010/0318002 A1 | 12/2010 | Prus et al. | |
| 2011/0034912 A1* | 2/2011 | de Graff | A61B 5/01 606/21 |
| 2012/0289869 A1 | 11/2012 | Tyler | |
| 2013/0046229 A1 | 2/2013 | Konofagou et al. | |
| 2014/0114216 A1 | 4/2014 | Konofagou et al. | |
| 2014/0264660 A1 | 9/2014 | Rothberg et al. | |
| 2014/0364774 A1 | 12/2014 | Mishelevich | |
| 2015/0065871 A1 | 3/2015 | Konofagou et al. | |
| 2016/0287909 A1* | 10/2016 | Maxwell | A61B 8/0866 |

OTHER PUBLICATIONS

Liu et al., "Blood-Brain Barrier Disruption with Focused Ultrasound Enhances Delivery of Chemotherapeutic Drugs for Glioblastoma Treatment," Radiology 255(2):415-425 (2010).

Marquet et al., "Real-Time, Transcranial Monitoring of Safe Blood-Brain Barrier Opening in Non-Human Primates," PLoS One 9(2):e84310 (2014).

Salgaonkar et al., "Passive cavitation imaging with ultrasound arrays," Journal of the Acoustic Society of America, 126(6):3071-3083 (2009).

* cited by examiner

SYSTEMS AND METHODS FOR MODULATION AND MAPPING OF BRAIN TISSUE USING AN ULTRASOUND ASSEMBLY

CROSS-REFERENCE TO RELATED APPLICATIONS

This application is a continuation of International Patent Application No. PCT/US2016/040776, filed Jul. 1, 2016, which claims priority to U.S. Provisional Application No. 62/187,639 filed Jul. 1, 2015, each of which is incorporated herein by reference in its entirety.

STATEMENT REGARDING FEDERALLY SPONSORED RESEARCH

This invention was made with government support under grants EB009041 and AG038961 awarded by the National Institutes of Health and by HR0011-15-2-0054 awarded by DOD/DARPA. The government has certain rights the invention.

BACKGROUND

Focused ultrasound can be used for non-invasive treatment of brain tissue, for example, via surgical ablation, blood-brain barrier (BBB) opening and drug delivery, and neuromodulation. Certain neurological disorders and neurodegenerative diseases can be difficult to treat due at least in part to the impermeability of the blood-brain barrier, and thus, focused ultrasound can be effective to open the blood-brain barrier to induce the diffusion of molecules into brain tissue. Such methods can be used to treat Central Nervous System (CNS) diseases, including Alzheimer's Disease, and neurodegenerative diseases, such as Parkinson's Disease and Huntington's Disease.

A repetitive course of focused ultrasound treatment can be used to provide, for example, consistent drug delivery or neuromodulation. However, certain systems for focused ultrasound can utilize bulky and immovable equipment that can be unsuitable for use outside of a clinical setting. Additionally, it can be necessary to monitor the focused ultrasound throughout treatment to ensure efficacy and patient safety, which can further increase the size or complexity of such equipment.

Therefore, there remains an opportunity for improved techniques for modulation and mapping of brain tissue that can be more convenient and simpler for the patient, including for use by the patient outside of a clinical setting, while providing safe and effective treatment.

SUMMARY

The presently disclosed subject matter provides techniques for modulation and mapping of brain tissue in a subject using an ultrasound assembly. An exemplary method for modulation uses a wearable ultrasound assembly including a housing configured to be secured to the head of the subject and an ultrasound transducer joined to the housing. The method includes securing the housing to the head of the subject with the ultrasound transducer aligned with a region of the brain tissue to target the region of the brain tissue for modulating, and providing focused ultrasound at an acoustic pressure to the targeted region using the ultrasound transducer to induce cavitation proximate the targeted region. The method further includes detecting a cavitation signal magnitude from the induced cavitation corresponding to the acoustic pressure and modulating the targeted region.

As embodied herein, the method can further include mapping the cavitation signal magnitude and comparing the cavitation signal magnitude to a threshold cavitation signal magnitude. For example, and as embodied herein, the modulation and mapping can be performed substantially simultaneously. The brain tissue can be mapped with neuronavigation and the region of the brain tissue can be targeted based on the neuronavigation. Mapping the brain tissue can include imaging the brain tissue. Microbubbles can be introduced to the targeted region. The targeted region can be modulated to a predetermined target value without the cavitation signal magnitude exceeding the threshold cavitation signal magnitude. As embodied herein, the microbubbles can have a diameter within a range of about 4 μm to about 5 μm. The microbubbles can be provided to the subject in a solution via intravenous injection.

The method can further include modulating the acoustic pressure in real time based on the cavitation signal magnitude. The acoustic pressure can be less than an acoustic pressure corresponding to an unsafe cavitation signal magnitude. Detecting the cavitation signal magnitude can include measuring and mapping the cavitation signal magnitude in real time and displaying the cavitation signal magnitude.

As embodied herein, and without limitation, the targeted region can be within brain tissue corresponding to the hippocampus, basal ganglia, motor cortex, somatosensory cortex, putamen, amygdala, dorsal anterior cingulate cortex (dACC), subthalmic nucleus (STN), or dorsal striatum (DS). The subject can be suffering from Alzheimer's Disease, Parkinson's Disease, Huntington's Disease, Amyotrophic Lateral Sclerosis (ALS), Obsessive Compulsive Disorder (OCD), schizophrenia, depression, addiction, or stroke.

The presently disclosed subject matter also provides systems for modulation of brain tissue in a subject. An exemplary system can include an ultrasound assembly including a housing configured to be secured to the head of the subject and an ultrasound transducer joined to the housing for providing focused ultrasound at an acoustic pressure to a targeted region in the brain tissue to induce cavitation proximate the targeted region. The system can further include a passive cavitation detector for detecting a cavitation signal magnitude from the induced cavitation corresponding to the acoustic pressure, and one or more processors for controlling the wearable ultrasound assembly and/or the passive cavitation detector.

As embodied herein, one or more processors can be configured to map the cavitation signal magnitude and compare the cavitation signal magnitude to a threshold cavitation signal magnitude. For example, and as embodied herein, the ultrasound assembly can be configured as a wearable ultrasound assembly. The wearable ultrasound assembly can include two or more flexible circuits, each including one or more transducers configured to be operated as an ultrasound transducer and a passive cavitation detector. Each of the transducers can include a piezoelectric material. The flexible circuits can be disposed on a printed circuit board tethered to the wearable ultrasound assembly. Each flexible circuit can further include a power amplifier and phase modulator for each transducer. The flexible circuits can include a thinned CMOS chip. The wearable ultrasound assembly can further include one or more EEG sensors tethered to the wearable ultrasound assembly. The wearable ultrasound assembly can further include one or more securing features for aligning the ultrasound transducer with respect to the targeted region.

For example, and as embodied herein, the ultrasound transducer can have a frequency within a range of about 500 kHz to about 1.5 MHz. The targeted region can have a size of about 2.6 mm laterally and about 16.7 mm axially. The system can further include a microbubble delivery system for introducing microbubbles. The microbubbles can have a diameter within a range of about 4 μm to about 5 μm. The microbubble delivery system can include a device for intravenous injection of a solution of the microbubbles. The system can further include a display for displaying the mapped cavitation signal magnitude in real time.

The presently disclosed subject matter also provides systems for modulation of brain tissue in a subject including a wearable ultrasound assembly. The wearable ultrasound assembly can include a housing configured to be secured to the head of the subject and one or more flexible circuits including two or more transducers including a piezoelectric material joined to the housing for providing focused ultrasound at an acoustic pressure to a targeted region in the brain tissue to induce cavitation proximate the targeted region and for detecting a cavitation signal magnitude from the induced cavitation corresponding to the acoustic pressure. The system can further include two or more EEG sensors joined to the wearable ultrasound assembly for detecting a neuronal signal and one or more processors configured to control the ultrasound assembly and/or the transducers.

As embodied herein, one or more processors can be configured to map the cavitation signal magnitude and neuronal signal and compare the cavitation signal magnitude to a threshold cavitation signal magnitude. The flexible circuit can include a CMOS chip. Each of the flexible circuits can be disposed on a printed circuit board tethered to the wearable ultrasound assembly. Each flexible circuit can further include a power amplifier and phase modulator for each transducer.

DETAILED DESCRIPTION

The presently disclosed subject matter provides techniques for modulation and mapping in the brain tissue of a subject using an ultrasound assembly.

Figure 1:
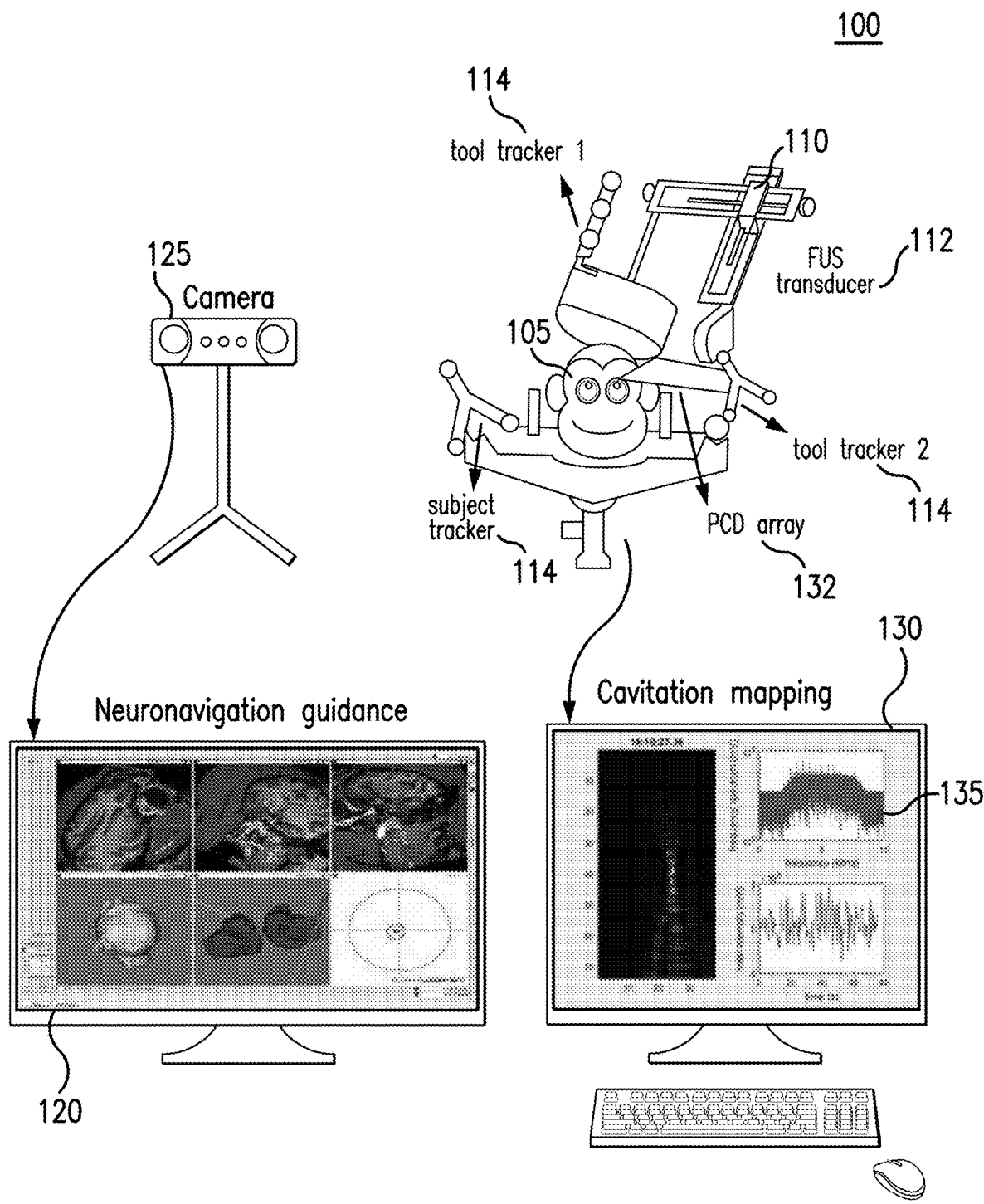
FIG. 1 is a diagram illustrating an exemplary embodiment of a system for modulation and mapping of brain tissue in a subject using an ultrasound assembly according to the disclosed subject matter.

According to aspects of the disclosed subject matter, systems and techniques for modulation of brain tissue in a subject using an ultrasound assembly are provided. For the purpose of illustration and not limitation, FIG. 1 is a diagram illustrating an exemplary system according to the disclosed subject matter. Exemplary systems can include various combinations of some or all of the components of FIG. 1 according to the desired application(s) and are not limited to the particular combinations of components described herein.

With reference to FIG. 1, an exemplary system 100 can include an ultrasound assembly 110. As embodied herein, an ultrasound assembly in accordance with the disclosed subject matter can include a housing that is configured to be secured with respect to the head of a subject 105. For example, the subject can be secured prior to providing focused ultrasound in order to stabilize a target region for the focused ultrasound.

Figure 2:
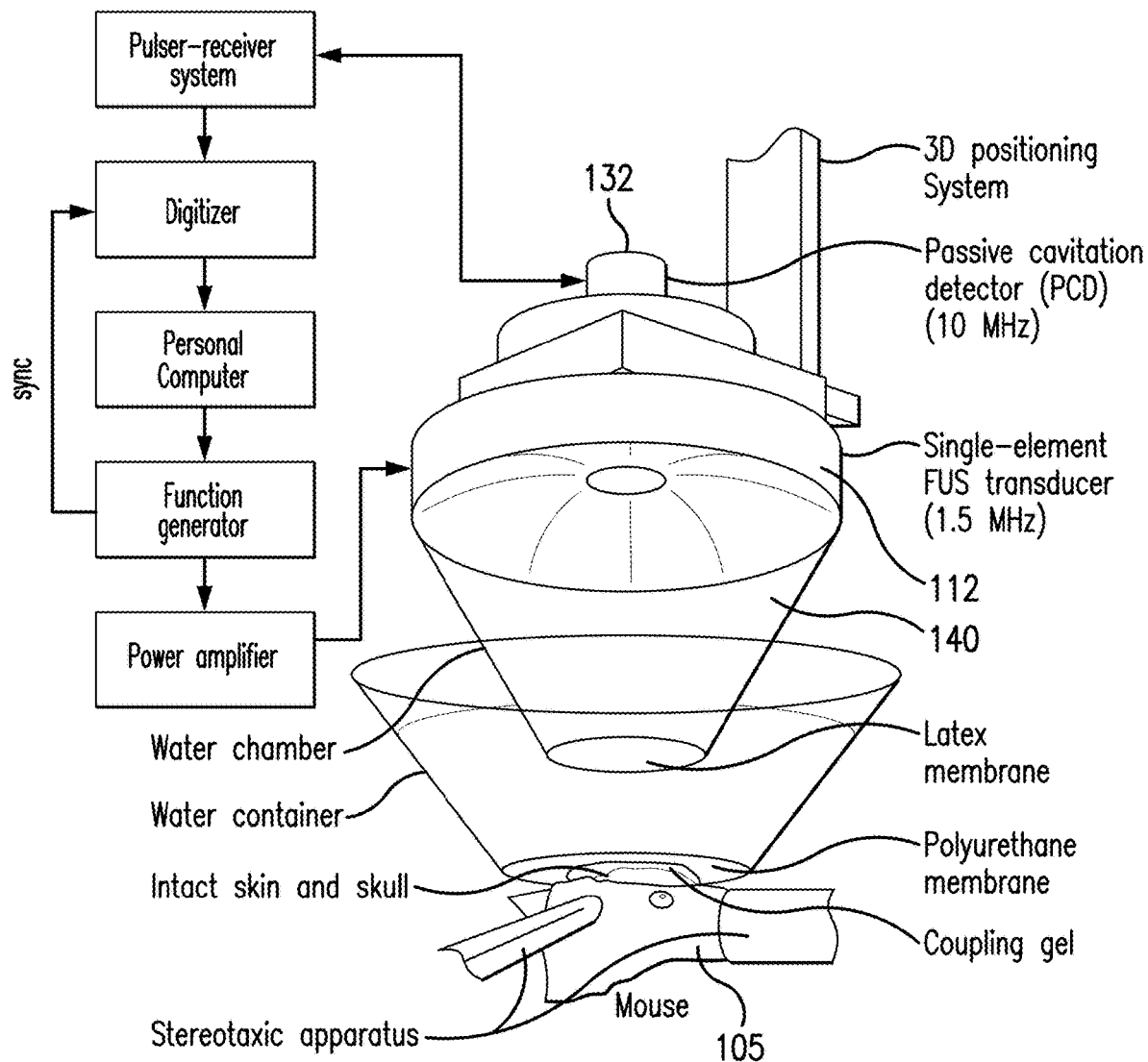
FIG. 2 is a diagram illustrating additional details of the ultrasound assembly of an exemplary embodiment of a system for modulation and mapping of brain tissue in a subject according to the disclosed subject matter.
Figure 3:
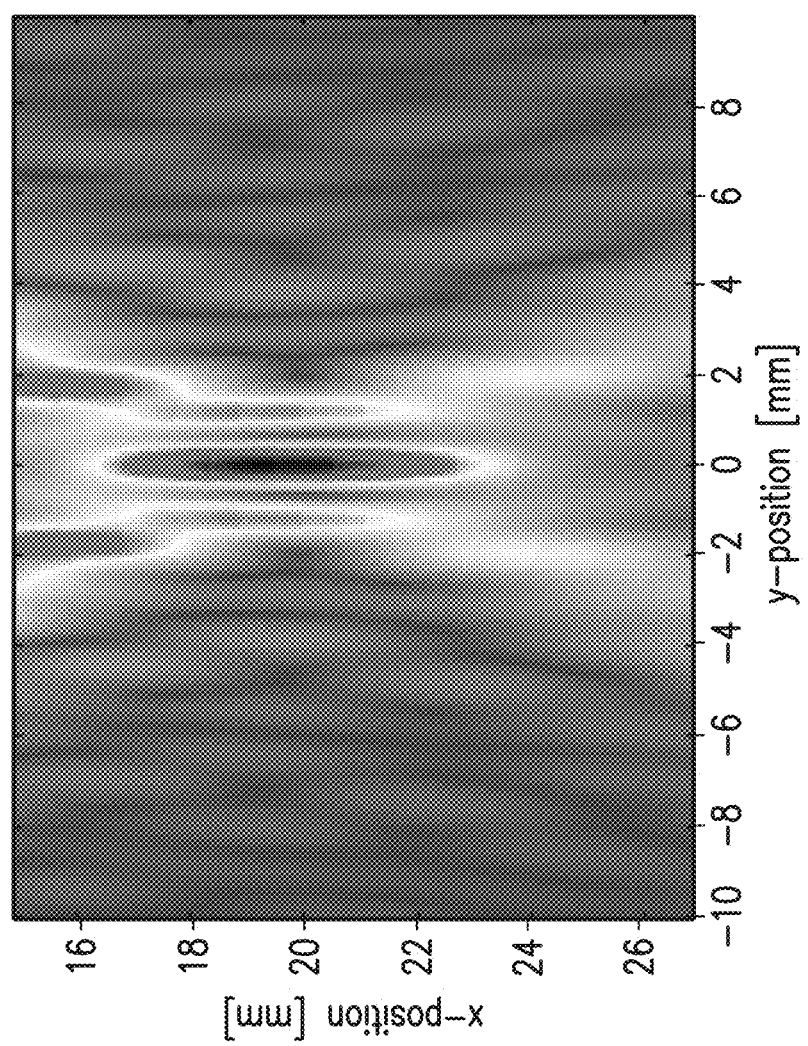
FIG. 3 is a graph illustrating an exemplary focused ultrasound beam in water.

As embodied herein, the ultrasound assembly 110 can further include an ultrasound transducer 112 joined to the housing. The ultrasound transducer can be configured to provide focused ultrasound to the subject 105 during treatment. For the purpose of illustration and not limitation, additional details of the ultrasound transducer, as embodied herein, are provided in FIG. 2. As shown in FIG. 2, the ultrasound transducer 112 can be positioned relative to the subject 105 and provide a focused ultrasound through a medium 140, such as water. For example, and not limitation, the ultrasound transducer can be a single-element ultrasound transducer. Focused ultrasound can be provided by a concave transducer that is configured to provide a single, millimeter-sized geometric focus. With reference to FIG. 3, which provides a plot of a focused ultrasound beam in water, the area of the focused ultrasound can be localized and millimeter-sized. As embodied herein, the ultrasound transducer can include one or more piezoelectric elements capable of transmitting ultrasound waves.

By way of example, and not limitation, an exemplary ultrasound transducer can be a single-element, spherical-segment transducer (e.g., Imasonic, Voray sur l'Ognon, France) having a center frequency of 1.5 MHz, a focal depth of 60 mm, and a diameter of 60 mm. The ultrasound transducer can be driven by a function generator (e.g., 33220A, Agilent, Santa Clara, Calif.) through a 50-dB power amplifier (e.g., 325LA, E&I, Rochester, N.Y.). A cone-shaped chamber filled with degassed and distilled water can be mounted on the ultrasound assembly and sealed with an acoustically transparent latex membrane. The ultrasound transducer can be attached to a computer-controlled, three-dimensional positioning system (e.g., Velmex Inc., Bloomfield, N.Y.). The distance from the skull can be determined using pulse-echo imaging to determine the appropriate placement of the ultrasound transducer relative to the target region.

Alternatively or additionally, and with reference to FIG. 1, the ultrasound assembly 110 can include one or more trackers 114 for moving the ultrasound transducer 112 and/or subject 105 relative to each other. For example, and not limitation, one or more trackers 114 can position the ultrasound transducer 112 and/or subject 105 in three-dimensions to align the ultrasound transducer with a target, such as targeted region of the subject's brain. As embodied herein, the system can include a 3D positioning system for moving the ultrasound transducer relative to the subject. As embodied herein, the ultrasound assembly 110 can include multiple ultrasound transducers 112 such that ultrasound waves can be guided and positioned using beamforming techniques.

Referring still to FIG. 1, and as embodied herein, the system 100 can further include a neuronavigation system 120. For example, and not limitation, a neuronavigation system 120 can be used to map at least a portion of the subject's brain tissue before or during treatment with focused ultrasound. For example, a neuronavigation system 120 can be used to image at least a portion of the subject's brain tissue prior to treatment to map the brain tissue. By mapping the brain tissue prior to treatment, the treatment can be pre-planned. For example, and as embodied herein, the pre-planned treatment can be personalized for the subject based at least in part on the mapping.

Alternatively or additionally, the neuronavigation system 120 can be used to map at least a portion of the brain tissue during treatment. For purpose of illustration, and not limitation, the neuronavigation system can be used to guide the ultrasound transducer 112 during treatment. For example, and as embodied herein, the neuronavigation system 120 can be used during treatment to monitor and adjust the course of treatment, such as, and without limitation, the placement of the ultrasound transducer 112, the ultrasound frequency, duty cycle, a pulse length, a pulse repetition frequency, a burst length, a burst repetition frequency, burst count, a pressure range, a duration, and any other suitable parameters as known in the art, for example, as described in U.S. Patent Publication No. 2013/0046229A1 assigned to a common assignee, which is hereby incorporated by reference in its entirety. For example, information from the neuronavigation system 120 can be used to control the ultrasound transducer 112 and/or one or more trackers 114.

Any suitable technique can be used for neuronavigation. For purpose of illustration and not limitation, and as embodied herein, the neuronavigation system 120 can include one or more imaging devices (e.g., cameras) 125 for mapping the brain tissue. The imaging devices can use a variety of techniques, such as CT scanning, MRI, or positron emission tomography (PET). As embodied herein, functional MRI (fMRI) can be used in combination with an electroencephalogram (EEG) to map at least a portion of the brain tissue. In this manner, the neuronavigation system can collect and record electrical activity in the target region, as localized by fMRI. One or more EEG electrodes can be positioned on the subject in order to detect electrical activity.

As embodied herein, the use of fMRI in conjunction with EEG can provide improved temporal resolution and spatial selectivity. Additionally, fMRI can be used to hemodynamic response during focused ultrasound treatment. For example, neuronal activity can generate a hemodynamic response through a neurovascular coupling mechanism. Using fMRI the hemodynamic response induced by focused ultrasound can be compared to task-induced neuronal activity in the same brain region. Moreover, fMRI can be used to observe the entire brain while modulating only one target region, for example, to explore relationships among brain functions.

With continued reference to FIG. 1, the system 100 can further include a detection system 130 for detecting a cavitation signal magnitude, e.g., using a passive cavitation detector 132. For example, and not by way of limitation, a piezoelectric element can be operated in a passive mode to detect cavitation events. As embodied herein, a passive cavitation detector 132 can be joined to the ultrasound assembly 110. For example, and with reference to FIG. 2, the passive cavitation detector 132 can be joined to the housing of the ultrasound assembly 110 and disposed within a void defined by the ultrasound transducer 112. In this manner, the passive cavitation detector 132 can be embedded in the ultrasound assembly 110, and thus can be similarly portable and convenient while reducing the overall profile of the ultrasound assembly. The detection system can be used to monitor acoustic events, such as cavitation, during the focused ultrasound treatment. Additionally or alternatively, the detection system 130 can use MRI techniques, e.g., diffusion weighted MRI such as diffusion tensor imaging (DTI), to monitor safety and efficacy.

By way of example, and not limitation, a suitable detection system can be include a pulse-echo transducer having a center frequency of 10 MHz and a focal length 60 mm (e.g., Olympus, Waltham, Mass.) can be positioned through a central, circular hole of the ultrasound transducer such that their foci are aligned. The pulse-echo transducer can be driven by a pulser-receiver system (e.g., Olympus, Waltham, Mass.) connected to a digitizer (e.g., Gage Applied Technologies, Inc., Lockport, Ill.).

As embodied herein, the detection system 130 can further include a processor for collecting and storing information regarding the cavitation signal magnitude and visualizing said cavitation signal magnitude. For example, the processor can map the cavitation signal magnitude spatially and/or temporally. In certain embodiments, the cavitation signal magnitude can be mapped in real time such that system simultaneously modulates and maps brain tissue during treatment. As embodied herein, the detection system 130 can further include a display for visualizing the cavitation signal magnitude in real time.

Further, and as embodied herein, one or more outputs from the detection system 130 can be used in the neuronavigation system 120 to guide the ultrasound transducer 112 during treatment. For example, neuromodulation induced activity can be detected by EEG and localized using fMRI while monitoring safety using the detection system 130.

As embodied herein, the ultrasound assembly can be a wearable ultrasound assembly. A wearable ultrasound assembly can be used to treat a patient in a variety of locations, including outside of a clinical setting, and at any time and frequency. The wearable ultrasound assembly can be portable and/or can be used without assistance from a clinician. For example, and as embodied herein, certain conditions can be treated using frequent or regular treatments, and thus it can be desirable for the treatment to be performed outside a clinical setting, such as and without limitation, in the subject's home. Accordingly, focused ultrasound can be provided by a wearable ultrasound assembly when symptoms occur and/or pursuant to a predetermined regular schedule. The wearable ultrasound assembly can be pre-programmed with particular parameters to treat the subject's condition. Additionally or alternatively, the wearable ultrasound assembly can include an interface to permit the parameters to be adjusted, for example and without limitation, by the subject or by a clinician. For purpose of illustration and not limitation, the parameters can be adjusted according to the symptoms experienced by the subject. Such parameters can include the location, frequency, and acoustic pressure of the focused ultrasound.

Figure 4A:
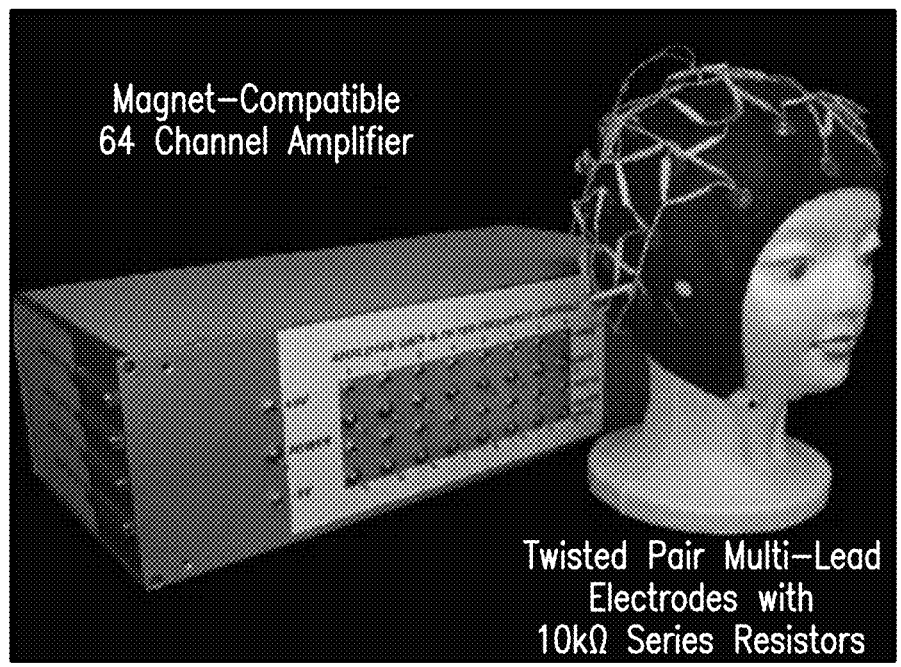
FIG. 4A is an image of an exemplary embodiment of a wearable ultrasound assembly.
Figure 4B:
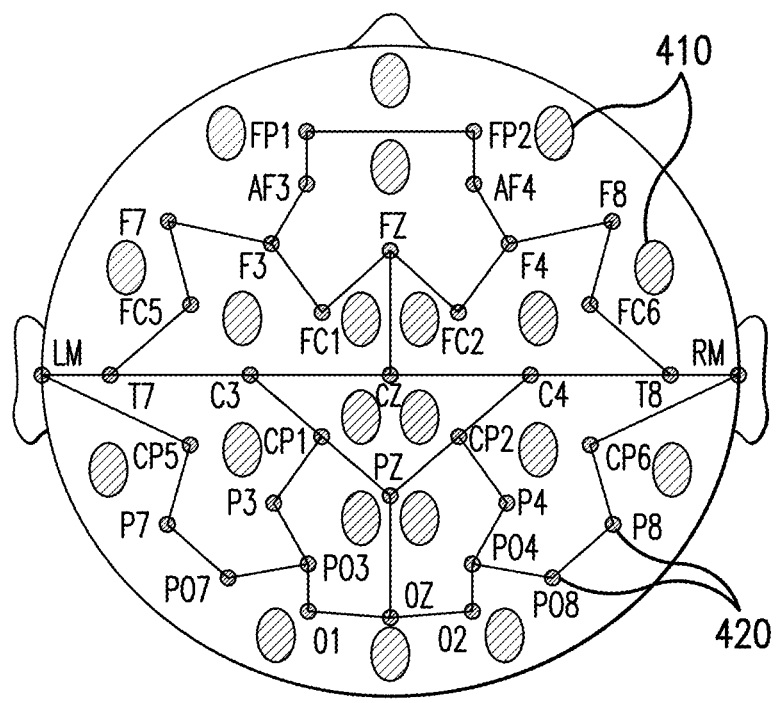
FIG. 4B is a schematic view of an exemplary embodiment of a wearable ultrasound assembly with multiple transducers and EEG sensors. Lines indicate connections to amplifiers and are wires that can be moved on the assembly.

As embodied herein, a wearable ultrasound assembly can guide and focus a focused ultrasound beam from an ultrasound transducer. Additionally, a wearable ultrasound assembly can detect and record neural activity, e.g., with EEG electrodes, and/or cavitation activity, e.g., with one or more transducers, such as piezoelectric transducer elements. For the purpose of illustration, and not limitation, FIGS. 4A-4B depict a wearable ultrasound assembly in accordance with the disclosed subject matter. The wearable ultrasound assembly can include one or more patches of flexible transducers 410. At least some of the transducers can provide the focused ultrasound while other transducers can be operated in passive mode for detecting cavitation events. For example, and not limitation, the wearable ultrasound assembly can include about 40 4×4 arrays, e.g., transducer patches. The arrays or patches can be phased collectively in order to focus the ultrasound output of multiple ultrasound transducers to target regions of about 3 mm at 500 kHz center frequencies and acoustic pressures of greater than 1 MPa. For example, the arrays or patches can be driven at different phases with different time delays to achieve constructive superposition of the pressure fields in the target region. Suitable piezoelectric materials can include, for example, and not limitation, polyvinylidene fluoride (PVDF).

As embodied herein, the transducers can be controlled using a phase-control technique based on a matching network at the interface of the transducer. The transducers can be tunable with input control bits that can be programmed before initiating the system and/or periodically updated as a result of calibration or monitoring. For example, and as embodied herein, time-multiplexed imaging can be used for cavitation detection using a pulsed waveform and for neuromodulation using a continuous waveform such that ultrasound can be focused based on the imaging results from the same transducers.

As embodied herein, field-programmable gate arrays (FPGAs) can be used in an application-specific integrated circuit (ASIC) for the wearable ultrasound assembly to limit the amount of external computing resources required. The circuit can be configured as a flexible circuit. For example, and not limitation, each piezoelectric element wearable ultrasound assembly can be designed on a thinned, flexible complementary metal-oxide semiconductor (CMOS) chip. By way of example, and as embodied herein, the CMOS chip can be about 1.5 cm by 1.5 cm. The multiple piezoelectric elements can be tightly integrated with the electronics in the flexible circuit to create a small form-factor device while ensuring careful phase control of the piezoelectric elements.

Additionally, one or more EEG sensors 420 can be positioned on the wearable ultrasound assembly as shown in FIGS. 4A-4B. The transducer patches 410 and sensors 420 can be tethered to a small external printed circuit board (PCB) that can be configured to provide power, data processing, and/or control circuitry to phase the transducers with respect to each other. The flexible circuit can further include electronics for data conversion and/or power amplifiers to reduce the number of wires required per transducer patch.

The wearable ultrasound assembly can further include various components for securing the subject with respect to the ultrasound transducer. For example and without limitation, the system can include one or more restraints, straps, buckles, elastic bands, tape, VELCRO®, or any other suitable securing features.

Figure 5:
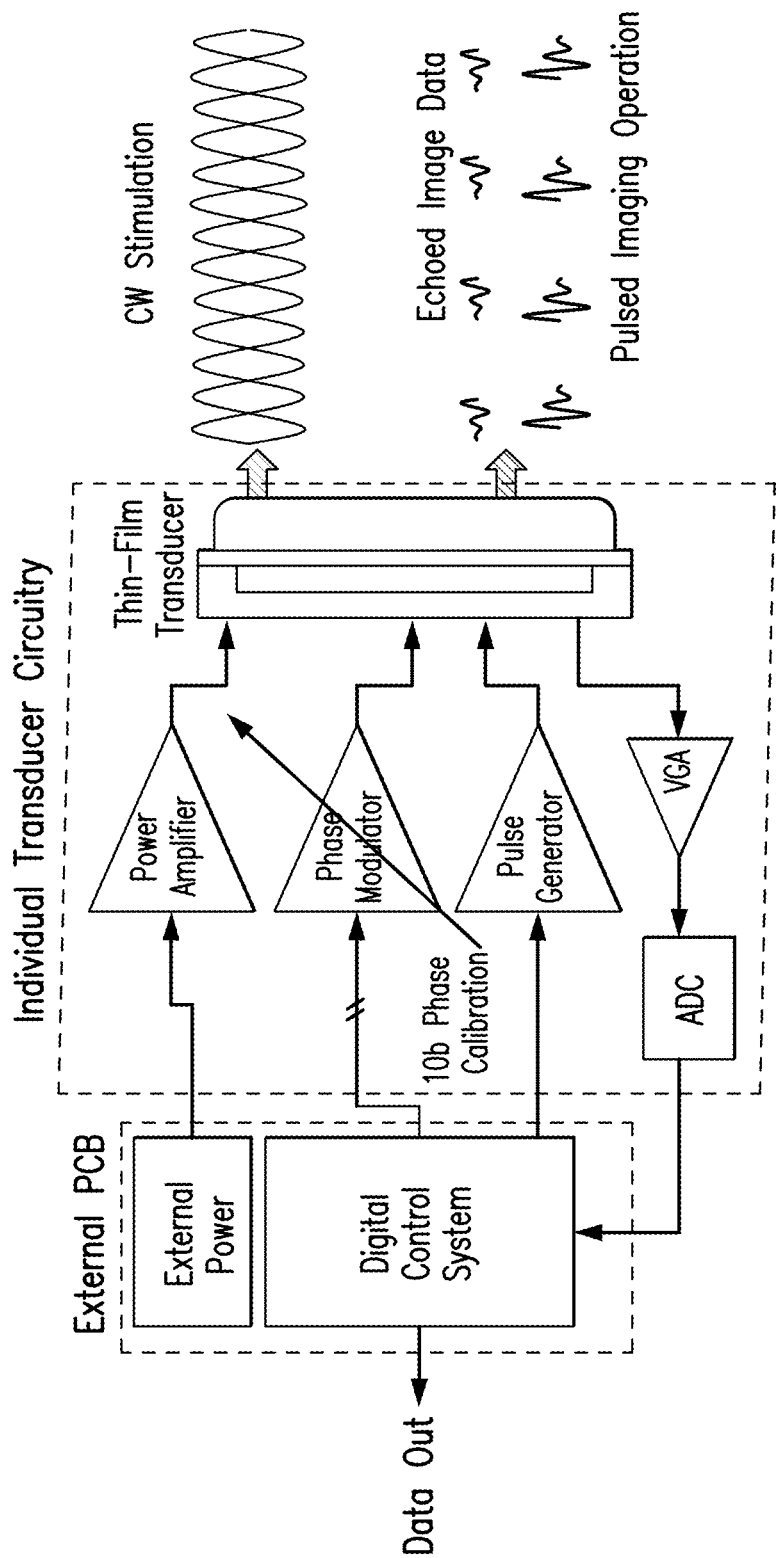
FIG. 5 is a system block diagram of a transducer patch for an exemplary embodiment of a wearable ultrasound assembly in accordance with the disclosed subject matter.
Figure 6:
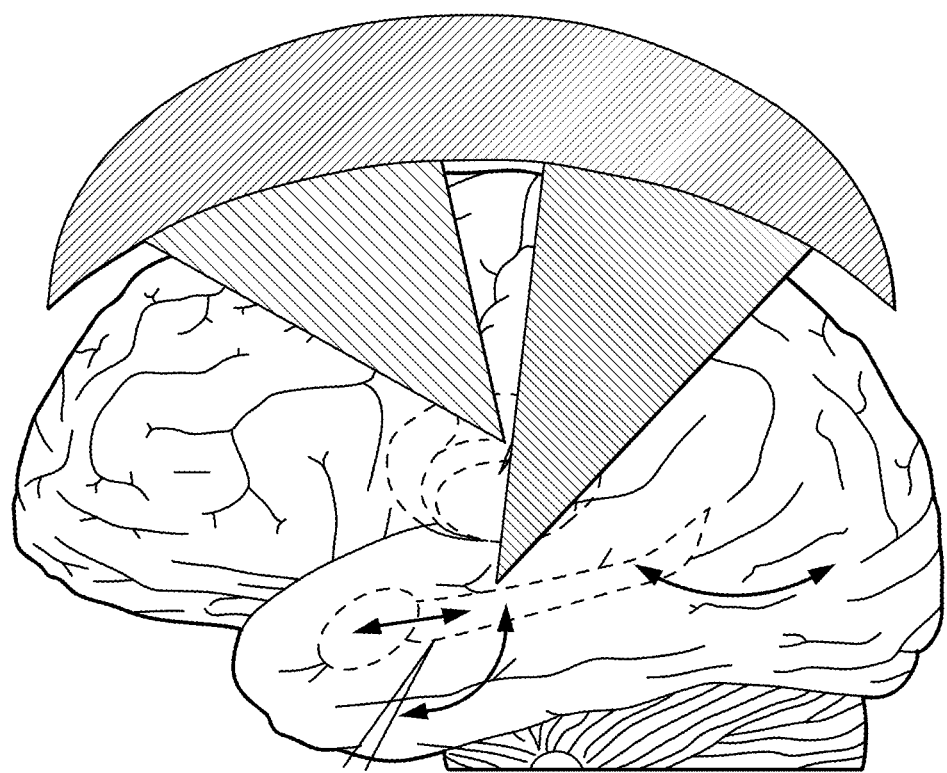
FIG. 6 is a schematic illustration of the phased array focusing capabilities of an exemplary embodiment of a wearable ultrasound assembly at shallower and deeper regions of the brain.

As embodied herein, the wearable ultrasound assembly can be operated in different modes, including and without limitation a calibration mode and a modulation/detection mode. The same transducers can be used for each mode of operation. In calibration mode, pulsed excitation can be used to determine the correct phase conditions for focusing on the target region. For the purpose of example, and not limitation, a system block diagram for the transducer patch is shown in FIG. 5. Circuitry can be embedded directly in the flexible CMOS substrate for the transducer array and each transducer can have its own power amplifier with an associated phase modulator. For example, and not limitation, the phase modulator can be designed to have a resolution of less than 2°, to provide precise tuning and matching. The phase modulator can include a variable phase buffer with near-unity gain and having a tunable complex impedance. Phase and amplitude feedback can be used to control the driving circuits. Each of the individual patches can be phased collectively to focus the energy to a single target region or multiple target regions within the brain, as shown in FIG. 6. Focusing can be based at least in part on phasing and geometry, each of which can be calibrated.

Figure 7:
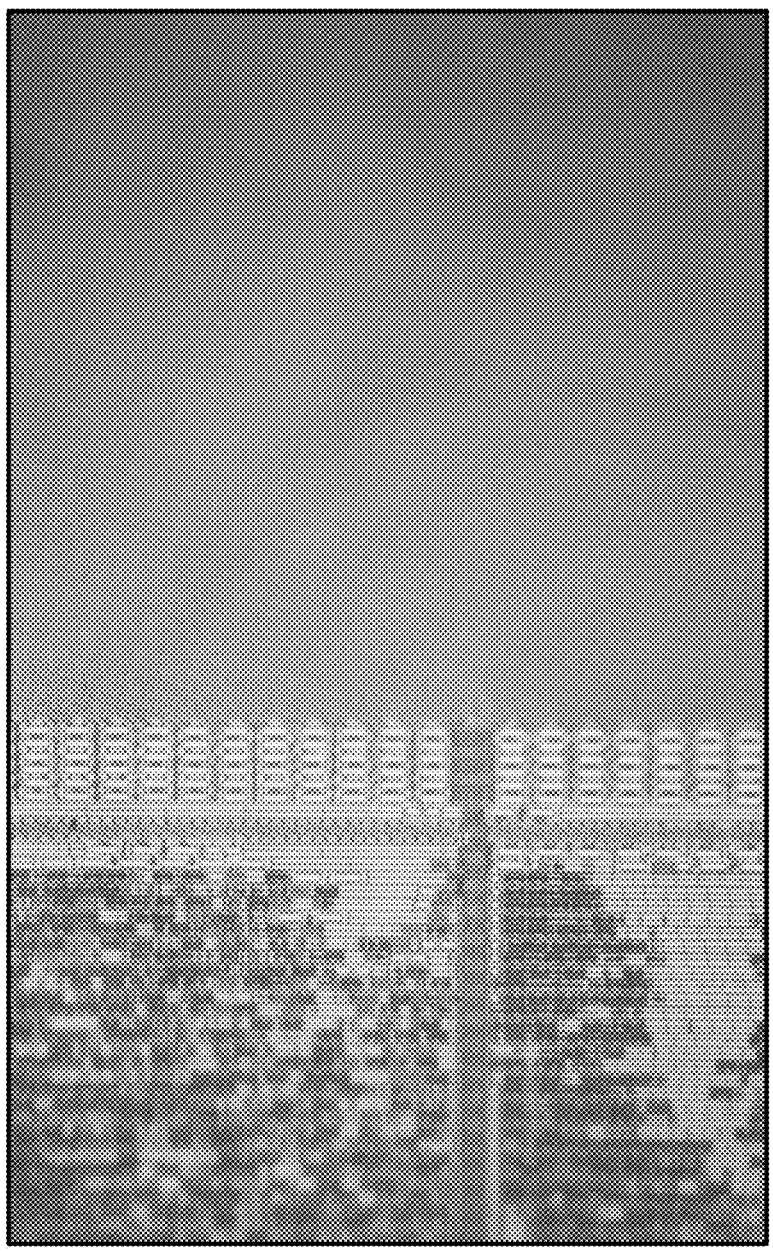
FIG. 7 is an image of the back view of an IBM 7RFSOI CMOS circuit after thinning to 2 μm.

The transducer array can be fabricated by chip thinning, integration of the piezoelectric transducer with the thinned chip and etching of the transducer for the individual transducer arrays on each patch. The top surface of the ASIC chip can be planarized with chemical-mechanical polishing (CMP). Thus, the top metal pads of the ASIC chips can be used as the bottom electrodes for the piezoelectric transducer. The top electrode, which can also serve as an etch mask for the piezoelectric material, can be deposited and patterned lithographically. Using the metal mask, the piezoelectric material can be patterned by wet etching and/or dry etching. A flexible CMOS chip can be created by thinning a conventional CMOS chip, which can reduce or minimize acoustic interference with the piezoelectric transducers. The thinning process can use, for example, wet etching and/or controlled spalling. For example, and not limitation, the thinning process can be based on a wet etching process with a buried-oxide layer as an etch stop. For the purpose of example, FIG. 7 shows an IBM CMOS7RF SOI circuit (viewed from the back) that has been thinned to 2 μm. The chip can remain flat after thinning as internal stresses can be low enough to avoid curling or bending. The flexibility of a thinned silicon circuit is determined, at least in part, by the minimum radius of curvature that can be sustained without material failure. For example, for a thickness of 2 µm, a bending radius of 300 µm will result in a strain of 0.3%, which can be easily tolerated without material failure, as CMOS circuits have been shown to be functional with up to 1% strain.

Figure 8:
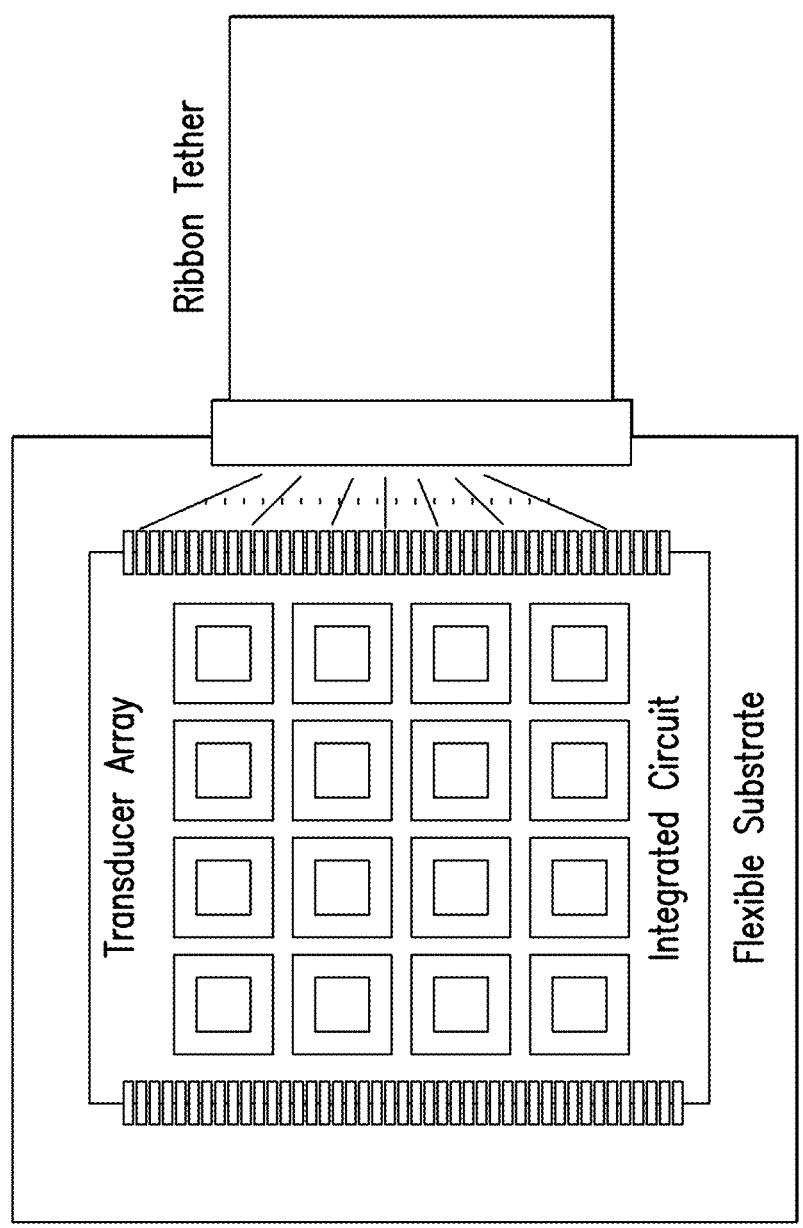
FIG. 8 is a schematic illustration of a top view of a CMOS circuit integrated on flexible PCB in accordance with the disclosed subject matter.

The transducer patches can be tethered to the wearable ultrasound assembly using a flexible printed circuit board (PCB) as a substrate, for example, a PCB based on KAPTON®. The flexible circuit can be embedded on the flexible PCB, creating a smooth surface across the surface of patch. The circuit can be mounted on the flexible PCB by bonding both face down onto a silicon carrier wafer. Metal interconnects between the PCB to the flexible circuit can be patterned and deposited. The flexible PCB can be further connected to a ribbon-cable interconnect such that the patch can be tethered to an external data acquisition board to combine the inputs from all the patches. For the purpose of example, and not limitation, FIG. 8 depicts a top view of the PCB after the flex-circuit integration process.

Additionally or alternatively, fMRI and/or EEG can be integrated into the wearable ultrasound assembly. For the purpose of example, and not limitation, a 34-electrode multi-lead twisted-pair cap of sensors and custom designed bipolar amplifiers can be integrated onto the wearable ultrasound assembly. A twisted-pair multi-lead system can be more robust to the complex artifacts generated in the EEG signals by the presence of a living subject in an MR scanner, e.g., due to the ballistocardiogram (BCG). For example, gradient induced artifacts can be easily removed because they are caused by the same current pulses in the gradient coils at each interval and can be accurately averaged and subtracted. Moreover, with the extra information from the multiple leads, the true EEG signals can be separated from the BCG. EEG and fMRI can be simultaneously recorded, for example and without limitation, and as embodied herein, using a Philips Achieva 3T MR scanner. Electrode impedances can be maintained at less than about 20 k$\Omega$, and can include resistors, such as 10 k$\Omega$ resistors to increase subject safety.

As embodied herein, EEG data can be preprocessed using software, such as MATLAB® (Mathworks, Natick, Mass.) with digital Butterworth filters, for example a 0.5 Hz high pass to remove DC drift, 60 Hz and 120 Hz notches to remove electrical line noise and its first harmonic, and 100 Hz low pass to remove high frequency artifacts not associated with neurophysiological processes. These filters can be applied together as a linear phase finite impulse response (FIR) filter to avoid distortions caused by phase delays. In addition to standard EEG artifacts, electrophysiological signals recorded inside the MRI scanner can include gradient and BCG artifacts due to magnetic induction in the EEG wires. In the open-loop case, gradient artifacts can be removed by subtracting the mean artifact across all functional volume acquisitions as a post-processing step. Additionally or alternatively, a 10 ms median filter can be used to remove any residual spike artifacts. BCG artifacts can be removed from the continuous gradient-free data using a principal components analysis (PCA) method in which the data are low-passed at 4 Hz to extract the signal within the frequency range where BCG artifacts are observed, and then the first two principal components extracted. The corresponding channel weightings can be subtracted out. The BCG-free data can be rereferenced to calculate scalp topographies of EEG discriminating components.

Additionally or alternatively, a Neuroelectromagnetic Forward Modeling Toolbox (NFT) can be used for EEG imaging, including EEG source localization and modeling. For example, the scalp, skull, cerebrospinal fluid (CSF), and brain tissues can be segmented from T1-weighted MR images and using the Boundary Element Method (BEM) for the numerical solution of the forward problem. Source dynamics can be estimated using the Source Information Flow Toolbox (SIFT). Both of these toolboxes can be integrated with the EEG processing.

Additionally, fMRI can be acquired using the same MR scanner with a FE echo-planar imaging (FE-EPI) sequence. However, EPI scans can be susceptible to field inhomogeneity, which can result in a geometric distortion and signal loss, e.g., caused by the presence of a subject with the wearable ultrasound assembly. As such, a magnetic field map can be measured to compensate for the effect of extra equipment inside the scanner.

According to other aspects, the presently disclosed subject matter provides techniques for modulation of brain tissue in a subject using an ultrasound assembly. As embodied herein, the ultrasound assembly can include some or all of the features described above, for example, a housing and an ultrasound transducer joined to the housing.

Figure 9:
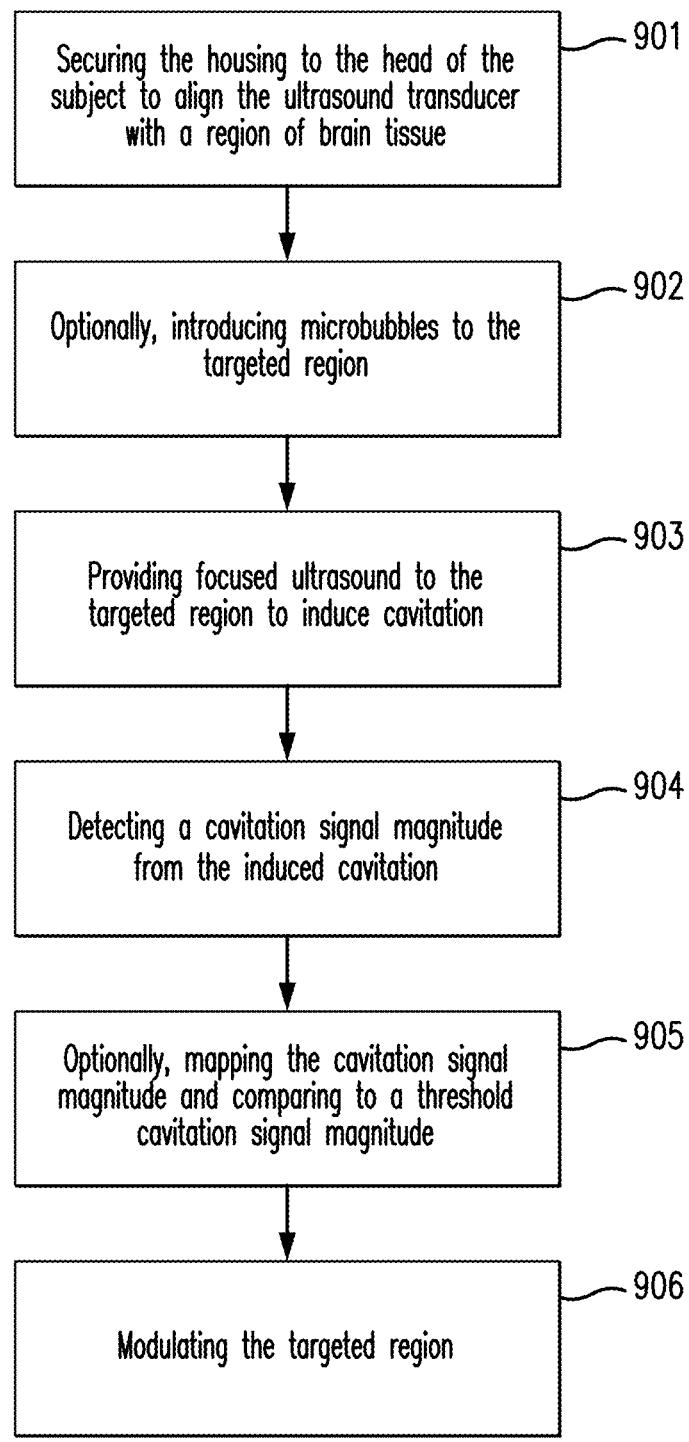
FIG. 9 is a diagram illustrating an exemplary method for modulation and mapping of brain tissue in a subject using an ultrasound assembly according to the disclosed subject matter.

For the purpose of illustration and not limitation, FIG. 9 provides an exemplary method for modulation of brain tissue using an ultrasound assembly in accordance with the disclosed subject matter. As illustrated in FIG. 9, the method 900 can include securing the housing of the ultrasound assembly to the head of a subject 901. For example, the housing can be secured such that the ultrasound transducer is aligned with a region of the brain tissue. In this manner, a region of the brain tissue can be targeted for neuromodulation and/or opening. In certain embodiments, securing the ultrasound assembly can include anesthetizing the subject.

As embodied herein, the presently disclosed methods can be used to target various regions of the brain, depending, for example, on the condition to be treated. For example, the region can correspond to brain tissue within the hippocampus, basal ganglia, motor cortex, somatosensory cortex, putamen, amygdala, dorsal anterior cingulate cortex (dACC), subthalmic nucleus (STN), and dorsal striatum (DS).

As embodied herein, the method can optionally include mapping the brain tissue with neuronavigation and targeting the region of the brain tissue based on the neuronavigation. For example, neuronavigation can be used prior to providing a focused ultrasound to the targeted region in order to plan the treatment. Additionally or alternatively, neuronavigation can be used to guide the focused ultrasound during treatment. As embodied herein, mapping the brain tissue with neuronavigation can include imaging the brain tissue. For example, the brain tissue can be imaged using a CT scan and/or an MRI.

With further reference to FIG. 9, the method 900 can optionally include introducing microbubbles to the targeted region 902. For example, and not limitation, microbubbles can be introduced to the subject via an intravenous injection. Microbubbles can be introduced prior to or during treating with focused ultrasound. The microbubbles can induce mechanical stress into the brain tissue. In certain embodiments, the microbubbles can temporarily open the blood-brain barrier.

As embodied herein, the microbubbles can have a diameter of less than or equal to 8 µm. For example and not limitation, the microbubbles can have a diameter from about 4 µm to about 5 µm. The microbubbles can be introduced in a solution at a certain concentration. For example, and not limitation, in particular embodiments, the solution includes microbubbles at a concentration of about $250 \times 10^6$ to $10^9$ microbubbles/kg.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

As embodied herein, the method 900 can further include providing focused ultrasound to the targeted region to induce cavitation 903. Focused ultrasound can be provided using an ultrasound transducer, e.g., a single-element ultrasound transducer. Ultrasound can refer to a sound wave having a frequency above that of human hearing, e.g., greater than 16 kHz. As such, the focused ultrasound for use in the presently disclosed subject matter can have a frequency greater than about 16 kHz, and as embodied herein, can be within a range from about 50 kHz to about 20 MHz. For example, and not limitation, the ultrasound transducer can provide an ultrasound at a frequency of about 500 kHz (i.e., 0.5 MHz), or about 1.5 MHz. Additionally, the focused ultrasound can be provided at a certain acoustic pressure. For example, and not limitation, the acoustic pressure can be from about 100 kPa to about 5000 kPa, or from about 200 kPa to about 2000 kPa. As embodied herein, the acoustic pressure can be selected to induce neuromodulation.

The presently disclosed methods and systems can be used to target the region of brain tissue. For example, and not limitation, the focused ultrasound can be provided to a selected focal zone within the targeted region. In certain embodiments, the focal zone within the targeted region can have a size of about 4 mm laterally and about 35.3 mm axially, or alternatively, about 2.6 mm laterally and about 16.7 mm axially. The focused ultrasound can penetrate to a selected focal depth. For example, and not limitation, the focal depth can be from about 20 mm to about 120 mm, or about 60 mm. As such, the focused ultrasound can penetrate both shallow and deep-seated regions of the brain tissue.

As embodied herein, the presently disclosed methods can be used to induce stable acoustic cavitation proximate the targeted region. The induced cavitation can provide neuromodulation to the targeted region. When used in conjunction with microbubbles, the induced cavitation can cause an opening within the targeted region. However, it can be desirable to monitor cavitation to detect unsafe or undesirable levels of cavitation, e.g., inertial cavitation, as will be appreciated by those of ordinary skill in the art. As embodied herein, the cavitation can correspond to the acoustic pressure of the focused ultrasound.

Thus, the method 900 can further include detecting a cavitation signal magnitude from the induced cavitation 904. For example, cavitation can be detected using a passive cavitation detector, as described above. The passive cavitation detector can include one or more transducers. By way of example, and not limitation, a transducer can passively receive cavitation emissions from the targeted region. Certain cavitation emissions can indicate the presence of cavitation. For example, broadband emissions can indicate the presence of inertial cavitation, whereas harmonic, subharmonic, or ultraharmonic emissions can indicate the presence of stable cavitation.

With continued reference to FIG. 9, the method 900 can optionally further include mapping the cavitation signal magnitude and comparing the cavitation signal magnitude to a threshold cavitation signal magnitude 905. The threshold cavitation signal magnitude can correspond to the present of unsafe or undesirable cavitation, for example, but not limited to, inertial cavitation. One or more parameters can be adjusted based on the cavitation signal magnitude. For example, the acoustic pressure can be reduced in order to reduce cavitation. Thus, the ultrasound transducer can provide focused ultrasound at an acoustic pressure that is less than the acoustic pressure corresponding to the threshold cavitation signal magnitude.

As embodied herein, the acoustic pressure can be modulated in real time based on the cavitation signal magnitude. For example, where the method is used for simultaneous modulation of brain tissue and mapping of the cavitation signal magnitude, the acoustic pressure can likewise be adjusted in real time based on the mapping. Moreover, mapping the cavitation signal magnitude can include displaying the cavitation signal magnitude, e.g., on a screen or other display.

With further reference to FIG. 9, the method 900 can further include modulating the targeted region 906. As embodied herein, the targeted region can be modulated to a predetermined target value. For example, and not limitation, the predetermined value can correspond to an acoustic pressure and/or an opening volume, if the tissue is to be opened. As embodied herein, the method can include detecting the modulation, e.g., using imaging such as MRI.

As mentioned above, the presently disclosed techniques can be used to provide focused ultrasound to a subject outside of a clinical setting, e.g., when symptoms occur and/or pursuant to a predetermined treatment schedule using a wearable ultrasound assembly. For example, a clinician can configure the wearable ultrasound assembly such that it is operable by the subject outside of a clinical setting. Configuring the wearable ultrasound assembly can include installing it outside of the clinical setting, for example, in the subject's home. The wearable ultrasound assembly can be configured to treat symptoms when they occur, for example, with certain parameters that can relieve or reduce the symptoms. In this manner, the subject can use the pre-configured wearable ultrasound assembly as needed. Alternatively, the clinician can determine a course of treatment and configure the wearable ultrasound assembly to be operated accordingly. Thus, the subject can use the pre-configured wearable ultrasound assembly pursuant to a schedule and/or for a set duration of time.

The presently disclosed methods and systems can be applied to a variety of living subjects, including humans and animals, and can be used to treat a variety of conditions. For example, the present disclosure can be used in the treatment of a Central Nervous System (CNS) disease, such as Alzheimer's Disease. Alternatively or additionally, the present disclosure can be used in the treatment of neurodegenerative diseases including Parkinson's Disease, Huntington's Disease, Amyotrophic Lateral Sclerosis (ALS), Obsessive Compulsive Disorder (OCD), schizophrenia, depression, and addiction. For further example, the present disclosure can be used in the treatment of movement disorders and pain syndromes, or for recovery from stroke or other cortical injuries. Moreover, although the description provides as an example opening the blood-brain barrier, the methods and systems disclosed herein are useful for neuromodulation without opening the blood-brain barrier or for opening other tissues, such as muscular tissue, liver tissue or tumorous tissue, among others.

EXAMPLES

For purpose of illustration and confirmation of the disclosed subject matter, and without limitation, exemplary techniques for modulation and mapping of brain tissue are further illustrated with reference to the examples below. Although the exemplary techniques are described with respect to a monkey subject, the techniques described herein can be applied to perform brain modulation and mapping in any subject, including other mammals and primates, such as humans.

Example 1

In this Example, neuronavigation was used to plan and guide focused ultrasound within the brain tissue of rhesus macaque subjects (non-human primates, or NHPs). In silico pre-planning of the focused ultrasound was performed based on CT scans and MRI.

Focused ultrasound was provided to brain tissue within the subcortical structure of the basal ganglia of three rhesus macaques. The subcortical structure of the basal ganglia can be associated with neurodegenerative diseases including Parkinson's and Huntington's disease. Both CT scans and MRI were performed to prepare personalized pre-planning and neuronavigation guidance (Brainsight, Rogue Research, Montreal, Quebec, Canada) for the focused ultrasound. For comparison, 3D numerical simulation of the acoustic pressure field was performed prior to and after opening of the blood-brain barrier using focused ultrasound. A single-element, 0.5-MHz focused ultrasound transducer (diameter: 64 mm) with in-house microbubbles were used for sonication. A programmable data acquisition system (Verasonics, Kirkland, Wash.) with an array of acoustic detectors was used for real-time passive cavitation mapping of both the location and intensity of cavitation events. Both the focused ultrasound and the cavitation mapping were guided with the neuronavigation system in real time during the ultrasound procedure. After sonication, a contrast enhanced T1-weighted MRI was used to confirm the location and size of the blood-brain barrier opening.

The accuracy of both the focused ultrasound targeting and cavitation mapping were validated both in silico and in vivo. The target shift averaged 2.0 mm laterally and 3.5 mm axially in the in vivo experiment. In silico, the shift due to the skull was predicted to be 0 to 1.0 mm laterally and 1.0 to 5.5 mm axially. Real-time cavitation mapping confirmed that the sonicated area with and without blood-brain barrier opening, and the distance between the centroid of the cavitation map and that of the resulting blood-brain barrier opening was less than 2 mm. In order to achieve the desired opening volume, the acoustic pressure and focal zone size in situ were estimated in silico and tailored for targeting in each subject. Simulation results showed a smaller focal zone size through the skull (2.6 mm laterally and 16.7 mm axially, compared with the original size of 4.0 mm laterally and 35.3 mm axially), which corresponded to the blood-brain barrier opening volume under specific peak negative pressures (NHP 1 at 200 kPa, NHP 2 at 600 kPa). The pressure difference between individual subjects was due to the difference in skull attenuation, since the in silico pressure reduction was estimated to be 30.9%±12.4% and 53.9%±14.3% in NHP 1 and NHP 2, respectively.

Accordingly, a neuronavigation-guided focused ultrasound system combining in silico pre-planning and real-time cavitation mapping is feasible can be used in blood-brain barrier opening and neuromodulation applications.

Example 2

In this Example, neuronavigation was used to plan and guide focused ultrasound within the brain tissue of three rhesus macaque subjects using the methods described in connection with Example 1. In silico pre-planning of the focused ultrasound was performed based on CT scans and MRI. The accuracy of both the focused ultrasound targeting and cavitation mapping were validated both in silico and in vivo.

Figure 10:
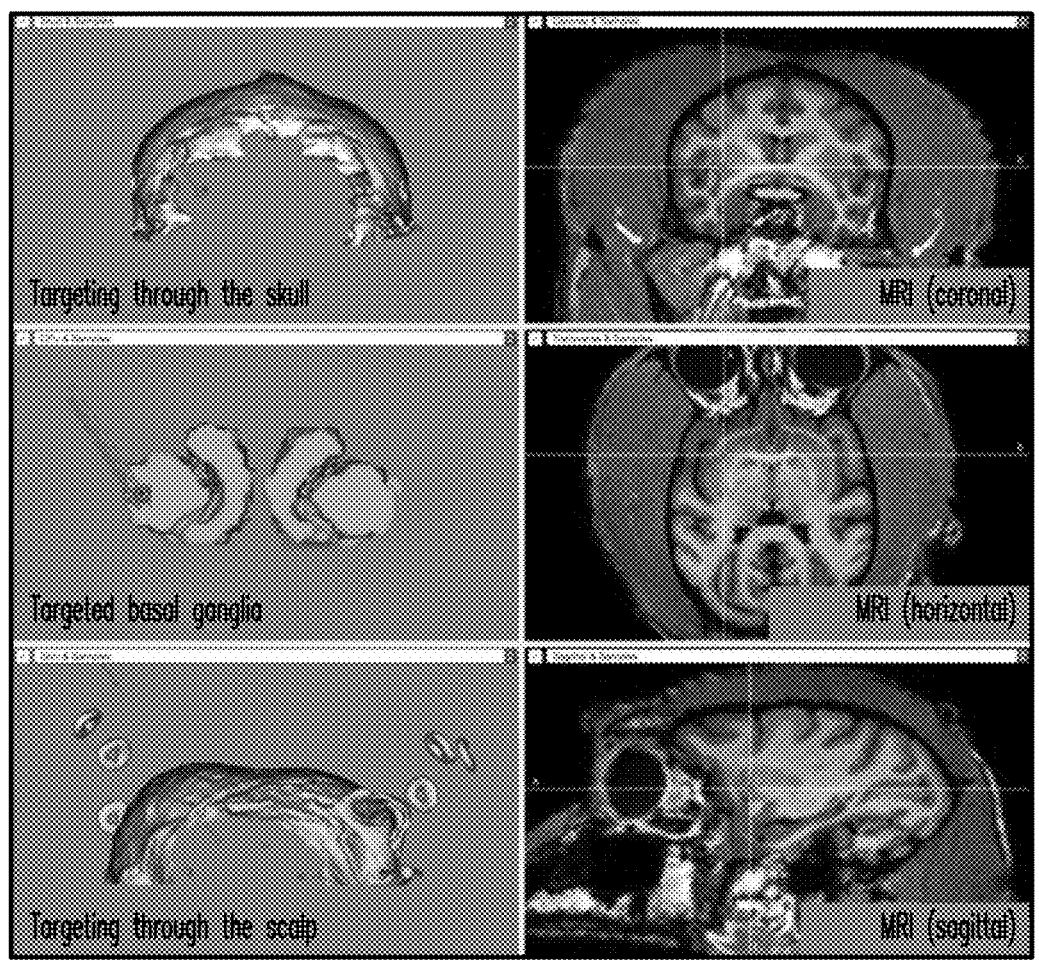
FIG. 10 is a screenshot of an exemplary neuronavigation system targeting the putamen in an anesthetized non-human primate (NHP).
Figure 11:
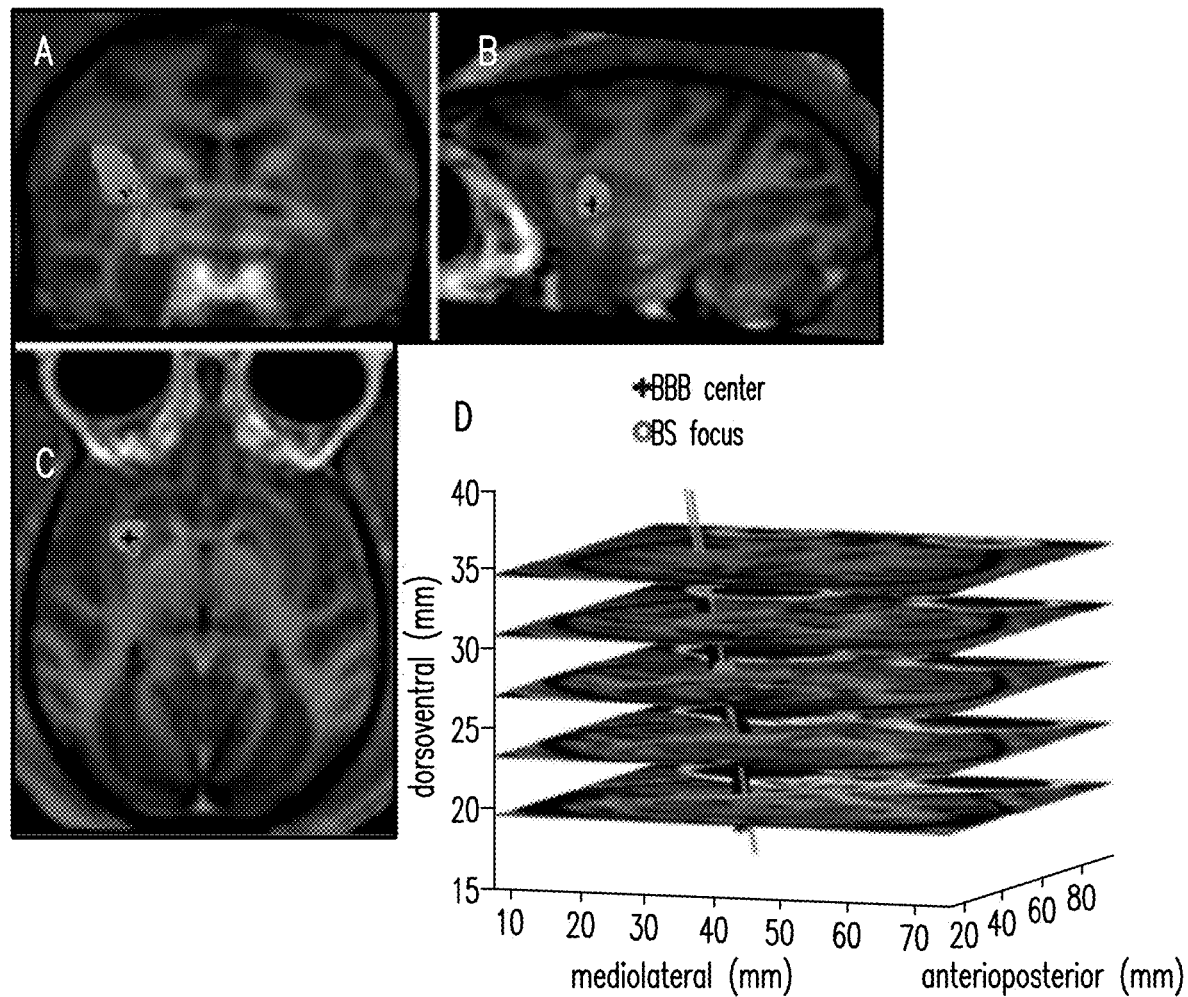
FIG. 11 is an image of a blood-brain barrier opening in an NHP of Example 2.
Figure 12:
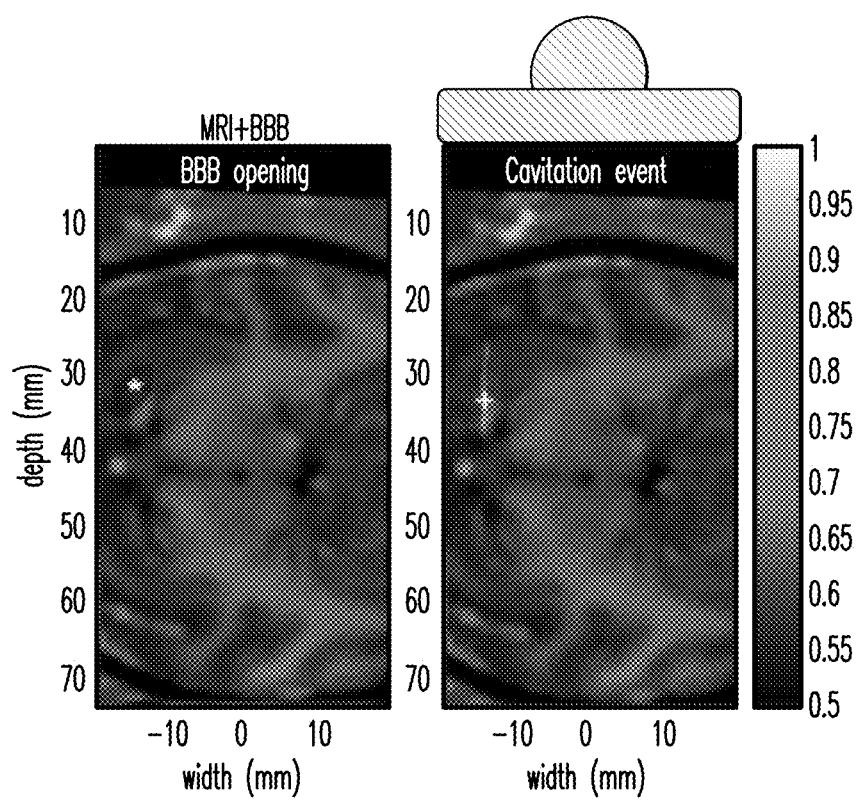
FIG. 12 is a cavitation map guided by neuronavigation in an NHP of Example 2.
Figure 13A:
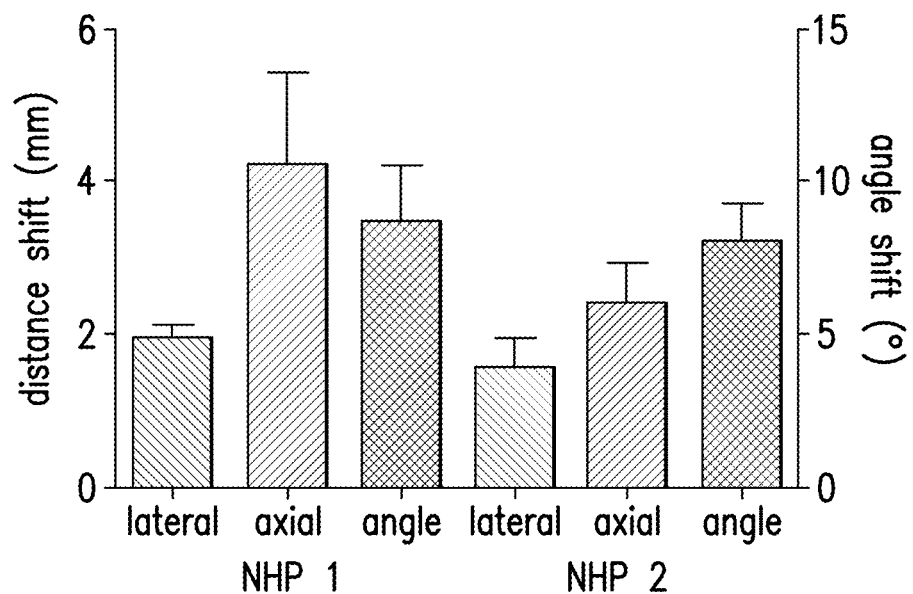
FIG. 13A is a graph of the target shift of the blood-brain barrier opening to the focus zone of the ultrasound in Example 2.
Figure 13B:
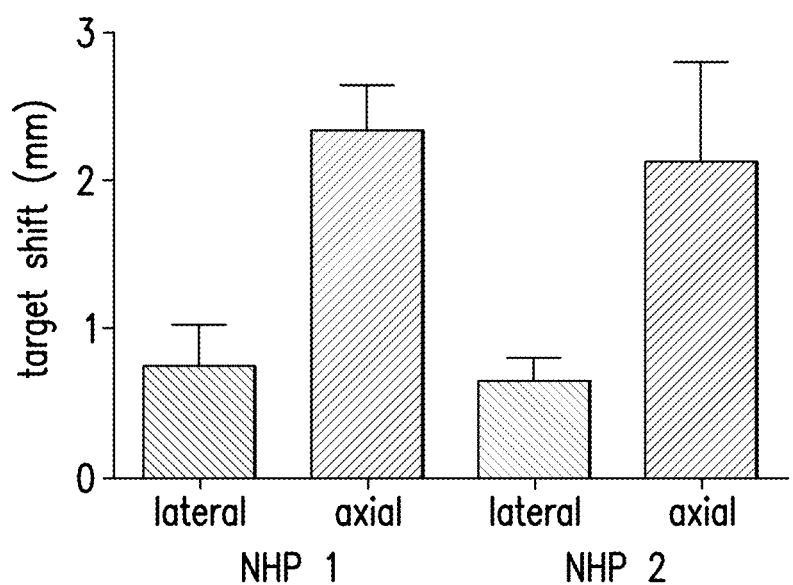
FIG. 13B is a graph of the target shift of the blood-brain barrier opening to the center of the cavitation event.

The ultrasound targeting was accurately guided by the neuronavigation system. A screen shot of this example neuronavigation system is shown in FIG. 10. FIG. 11 shows the blood-brain barrier opening. The cavitation events were visualized using cavitation mapping. As shown in FIG. 12, the cavitation map corresponded to the blood-brain barrier opening region. The overall targeting shift (FIG. 13A) was 1.54 to 1.76 mm laterally, 2.38 to 3.93 mm axially, and 8.66 to 8.10 in angle degree. Based on the cavitation mapping results, the distance between the center of cavitation and that of blood-brain barrier opening was 0.65 to 0.75 mm laterally and 2.14 to 2.34 mm axially (FIG. 13B). The target shift due to the skull was estimated to be 0.5 to 1.0 mm laterally and 0.5 to 5.3 mm axially.

Figure 14A:
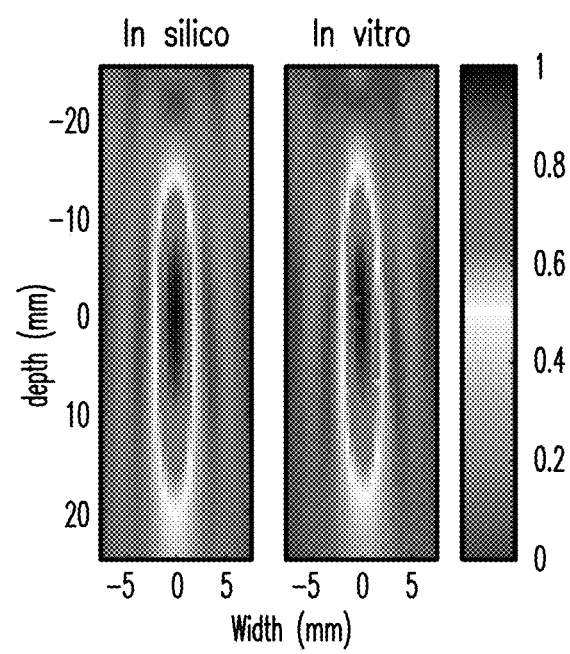
FIG. 14A is an image of the calibration of focus size in silico and in vitro.
Figure 14B:
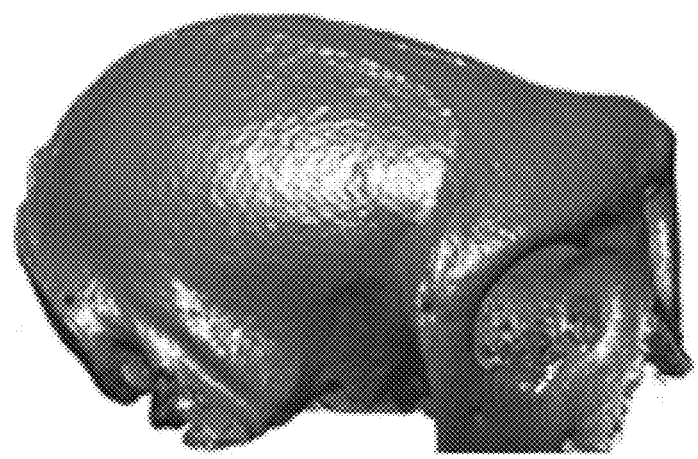
FIG. 14B is a CT scan of a rhesus macaque.
Figure 14C:
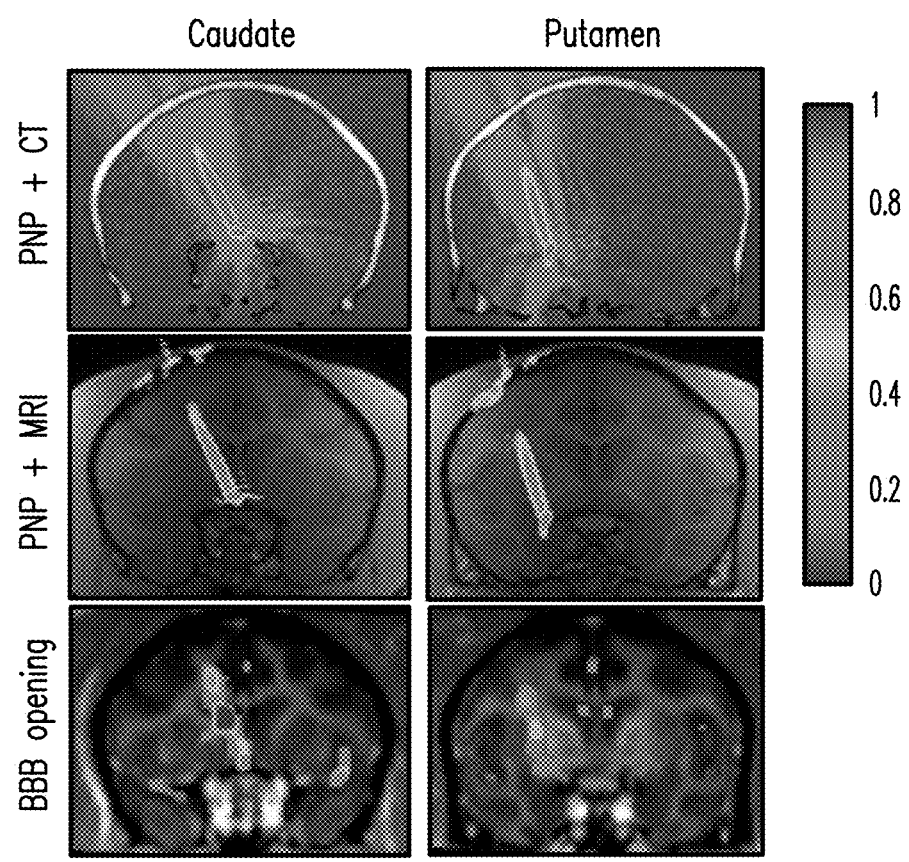
FIG. 14C is a graph of a simulated peak-negative pressure (PNP) field (normalized to the PNP without the skull).
Figure 15A:
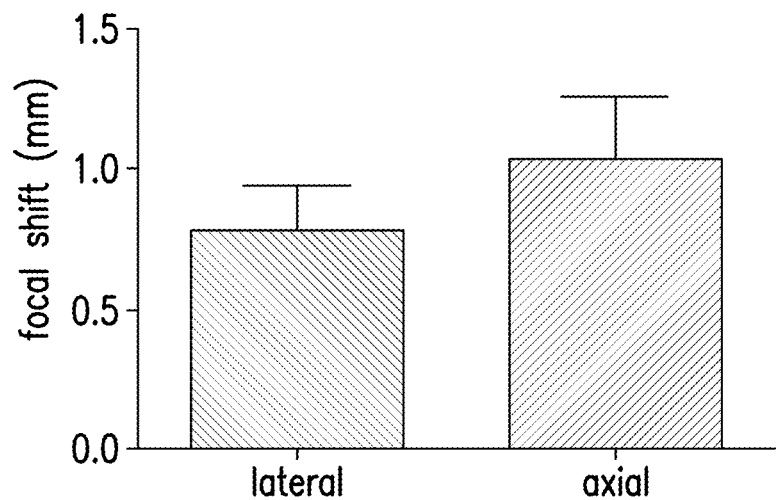
FIG. 15A is a graph of the acoustic focal shift due to the skull in the PNP field in both the lateral and axial directions.
Figure 15B:
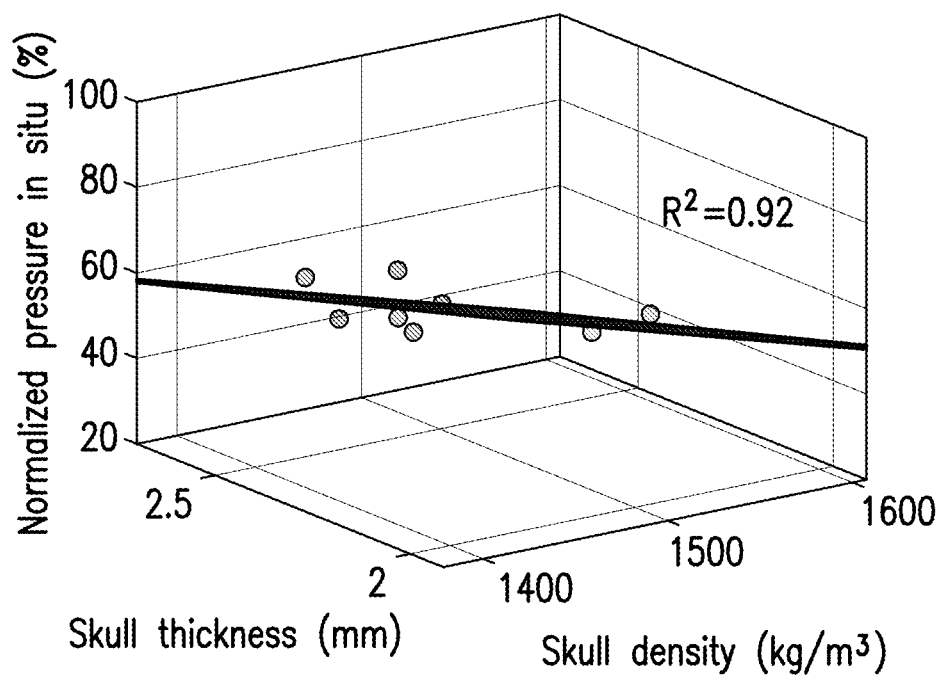
FIG. 15B is a graph of the estimated pressure reduction due to the skull and its correlation with skull thickness and density.

The location and volume of blood-brain barrier opening were in excellent agreement with the predicted pressure profile in situ. FIGS. 14A-14C shows the three-dimensional acoustic wave propagation through the skull in silico, where the focal size in silico was calibrated with the in vitro with hydrophone in water (FIG. 14A). A monkey CT scan (FIG. 14B) was acquired in order to extract skull properties, including the thickness and density, which was then transformed to the acoustic property such as speed of sound. The simulated peak-negative pressure (PNP) field (normalized to the PNP without the skull) was well-correlated with the blood-brain barrier opening both in terms of focal size and maximum pressure after the pressure was normalized to a threshold to 0.3 (FIG. 14C). Finally, the focal shift due to the skull aberration was found to be on the order of 1 mm in both lateral and axial direction (FIG. 15A) when targeting the putamen and the main cause of attenuation was attributed to the skull thickness as measured by the CT (FIG. 15B).

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the methods and systems of the disclosed subject matter without departing from the spirit or scope of the disclosed subject matter. Thus, it is intended that the disclosed subject matter include modifications and variations that are within the scope of the appended claims.

What is claimed is:

1. A system for modulation of brain tissue in a subject, comprising:
    a wearable ultrasound assembly comprising a housing configured to be secured to the head of the subject;
    at least one flexible circuit comprising two or more transducers including a piezoelectric material joined to the housing for providing focused ultrasound at an acoustic pressure to a targeted region in the brain tissue to induce cavitation proximate the targeted region and for detecting a cavitation signal magnitude from the induced cavitation corresponding to the acoustic pressure;

two or more EEG sensors joined to the wearable ultrasound assembly for detecting a neuronal signal; and one or more processors configured to control the ultrasound assembly and/or the transducers, wherein the one or more processors are configured to spatially map the cavitation signal magnitude and compare the cavitation signal magnitude to a predetermined threshold cavitation signal magnitude, wherein the one or more processors are configured to modulate the acoustic pressure based on the map of the cavitation signal magnitude for simultaneous modulation of the brain tissue.

2. The system of claim 1, wherein the flexible circuit comprises a CMOS chip.

3. The system of claim 1, wherein each flexible circuit is disposed on a printed circuit board tethered to the wearable ultrasound assembly.

4. The system of claim 1, wherein each flexible circuit further comprises a power amplifier and phase modulator for each transducer.

* * * * *